US007727190B2

(12) United States Patent
Miller (10) Patent No.: US 7,727,190 B2
(45) Date of Patent: Jun. 1, 2010

(54) ENVELOPING NEEDLE STICK PROTECTION DEVICE

(76) Inventor: Stuart H. Miller, 16 E. Eighth St., Clifton, NJ (US) 07011-1102

( * ) Notice: Subject to any disclaimer, the term of this patent is extended or adjusted under 35 U.S.C. 154(b) by 675 days.

(21) Appl. No.: 11/649,224

(22) Filed: Jan. 4, 2007

(65) Prior Publication Data

US 2008/0167611 A1    Jul. 10, 2008

(51) Int. Cl.
*A61M 5/00* (2006.01)
*A61M 5/32* (2006.01)

(52) U.S. Cl. ..................................... 604/110; 604/198

(58) Field of Classification Search ................. 604/110, 604/192–198, 181, 187, 263
See application file for complete search history.

(56) References Cited

U.S. PATENT DOCUMENTS

| | | | |
|---|---|---|---|
| 4,813,940 A | 3/1989 | Parry | |
| 5,106,379 A | 4/1992 | Leap | |
| 5,472,430 A | 12/1995 | Vaillancourt et al. | |
| 5,591,138 A | 1/1997 | Vaillancourt | |
| 5,795,336 A | 8/1998 | Romano et al. | |
| 5,984,899 A | 11/1999 | D'Alessio et al. | |
| 6,183,445 B1 | 2/2001 | Lund et al. | |
| 6,322,540 B1 | 11/2001 | Grabis et al. | |
| 6,325,781 B1 | 12/2001 | Takagi et al. | |
| 6,344,032 B1 | 2/2002 | Perez et al. | |
| 6,969,376 B2 | 11/2005 | Takagi et al. | |
| 2003/0144630 A1 | 7/2003 | Chang et al. | |
| 2005/0187522 A1* | 8/2005 | Miller | 604/198 |

* cited by examiner

*Primary Examiner*—Matthew F Desanto
(74) *Attorney, Agent, or Firm*—Welsh & Flaxman LLC (57) ABSTRACT

It is, therefore, an object of the present invention to provide a needle stick protection device. The device includes a housing shaped and dimensioned for positioning about a syringe with an attached needle. The housing includes a first housing member telescopically coupled to a second housing member. A locking member is associated with a first slot of the first housing member for selectively engaging a first detent to control positioning of the second housing member relative to the first housing member. The locking member includes a first lateral retaining recess formed within the first slot for seating of the first detent when the second housing member is in its forward most position, the first lateral retaining recess being circumferentially located along a side of the first slot. The needle may be selectively covered and uncovered by selective alignment of the first detent with the slot in manner permitting controlled motion of the first housing member relative to the second housing member. The locking member further includes a lateral locking recess formed along the slot and adjacent a second side of the spring biased lock arm opposite the first side of the spring biased lock arm, wherein the needle is permanently covered when the detent is positioned within the lateral locking recess.

18 Claims, 6 Drawing Sheets

ENVELOPING NEEDLE STICK PROTECTION DEVICE

BACKGROUND OF THE INVENTION

1. Field of the Invention

The invention relates to a device for preventing needle sticks. More particularly, the invention relates to a device for preventing needle sticks wherein the needle is selectively locked and released relative to a shielding device, and may ultimately be permanently locked once it is ready for disposal.

2. Description of the Prior Art

As those within the medical field have developed an understanding that a variety of diseases may be transferred via unclean and previously used needles, many devices have been developed for protecting medical practitioners and other individuals from previously used needles. Many currently available needle stick protection devices operate by either withdrawing the used needle into a hard protective shell or extending a hard protective shell over the used needle. These devices are generally utilized once and are then discarded in an approved collection device.

While most procedures permit the disposal of needles after a single usage, some medical procedures require that needles be used more than once during a procedure on a patient. However, these used needles may be passed between physicians and other medical practitioners several times during the procedure. As such, a possibility exists that physicians and other medical practitioners may be stuck with these used needles during the procedure.

A need, therefore, exists for a needle stick protection device in which the needle is selectively shielded and unshielded as the medical procedure dictates, and ultimately permanently locked in a shielded orientation once it is ready for disposal. The present invention provides such a needle stick protection device.

SUMMARY OF THE INVENTION

It is, therefore, an object of the present invention to provide a needle stick protection device. The device includes a housing shaped and dimensioned for positioning about a syringe with an attached needle. The housing includes a first housing member telescopically coupled to a second housing member. The first housing member includes an open first end shaped and dimensioned for receiving the syringe and attached needle and an open second end, the first housing member including a first longitudinally extending slot. The second housing member includes an open first end and a substantially closed second end. The second end includes an aperture shaped and dimensioned to permit the passage of a needle therethrough. The second housing member includes a first detent extending through the first slot. A locking member is associated with the first slot of the first housing member for selectively engaging the first detent to control positioning of the second housing member relative to the first housing member. The locking member includes a first lateral retaining recess formed within the first slot for seating of the first detent when the second housing member is in its forward most position, the first lateral retaining recess being circumferentially located along a side of the first slot. The locking member further includes a first spring biased lock arm composed of a cantilevered beam, which includes a first side that is adjacent to the first lateral retaining recess, wherein the spring biased lock arm circumferentially forces the first detent within the first lateral retaining recess when the second housing member is in its forward most position fully extended relative to the first housing member so that the needle is fully covered by the second housing member. The needle may be selectively covered and uncovered by selective alignment of the first detent with the slot in manner permitting controlled motion of the first housing member relative to the second housing member. The locking member further includes a lateral locking recess formed along the slot and adjacent a second side of the spring biased lock arm opposite the first side of the spring biased lock arm, wherein the needle is permanently covered when the detent is positioned within the lateral locking recess.

It is also an object of the present invention to provide a needle stick protection device wherein the spring biased lock arm includes a living hinge portion adjacent its free end creating a flexible tip at the free end of the spring biased lock arm which permits flexion of the tip about the living hinge portion in a manner allowing the detent to move from the first side of the spring biased lock arm to the second side of the spring biased lock arm.

It is also another object of the present invention to provide a needle stick protection device wherein the slot, on the first side of the spring biased lock arm, includes a first transverse surface, a first parallel surface, an oblique contact surface, a second transverse surface and a second parallel surface adjacent a tip of the spring biased lock arm.

It is also a further object of the present invention to provide a needle stick protection device wherein the oblique contact surface and the transverse surface defining the first lateral retaining recess.

It is another object of the present invention to provide a needle stick protection device wherein the second parallel surface prevents the tip from bending in a manner permitting the detent to move from the second side of the spring biased lock arm to the first side of the spring biased lock arm.

It is a further object of the present invention to provide a needle stick protection device wherein the slot, on the second side of the spring biased lock arm, includes a third transverse surface, a third parallel surface, as well as a fourth parallel surface and a fourth transverse surface defining the lateral locking recess.

It is still a further object of the present invention to provide a needle stick protection device including a spring positioned between the second end of the first housing member and the first end of the second housing member, the spring urging the first housing member and the second housing member to a fully telescoped position in which the needle is exposed.

It is yet another object of the present invention to provide a needle stick protection device wherein the second housing member further includes a slide actuating portion secured to the first detent of the second housing member facilitating controlled movement of the second housing member relative to the first housing member.

It is also an object of the present invention to provide a needle stick protection device wherein the housing is transparent.

It is another object of the present invention to provide a needle stick protection device wherein the first housing member further includes a second longitudinally extending slot and the second housing member further includes a second detent extending through the second slot.

It is a further object of the present invention to provide a needle stick protection device wherein the locking member further includes a second lateral retaining recess formed within the second slot for seating of the second detent when the second housing member is in its forward most position and a second spring biased lock arm biasing the second detent within the second lateral recess when the second housing member is in its forward most position.

It is also an object of the present invention to provide a needle stick protection device wherein the first and second spring biased lock arms are respective cantilevered beams.

It is also another object of the present invention to provide a needle stick protection device wherein the first housing member includes means for selectively attaching to a syringe.

It is also a further object of the present invention to provide a needle stick protection device wherein the means for selective attachment includes a pair of opposed slots at the first end of the first housing member, the opposed slots being shaped and dimensioned for receipt of the syringe.

It is also an object of the present invention to provide a needle stick protection device wherein the slide actuating portion is a thumb pad.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, a needle stick protection device 10 is disclosed. The needle stick protection device 10 includes a housing 12 shaped and dimensioned for positioning about a needle 14 and an associated syringe 16. The housing 12 includes a first housing member 18 telescopically coupled to a second housing member 20. The first housing member 18 includes an open first end 22 and an open second end 24. The first housing member 18 further includes slots 26a, 26b extending longitudinally along the length of the first housing member 18 along opposite sides of the first housing member 18.

The second housing member 20 includes an open first end 27 and a substantially closed second end 28. The second end 28 includes an aperture 30 shaped and dimensioned to permit the passage of the needle 14 therethrough. The second housing member 20 further includes detents 31a, 31b extending through the slots 26a, 26b for guiding the second housing member 20 relative to the first housing member 18 as the first and second housing members 18, 20 telescopically move relative to each other.

The needle stick protection device 10 also includes a locking member 32a, 32b associated with each of the slots 26a, 26b of the first housing member 18 for selectively engaging the detents 31a, 31b to control positioning of the second housing member 20 relative to the first housing member 18.

Figure 1:
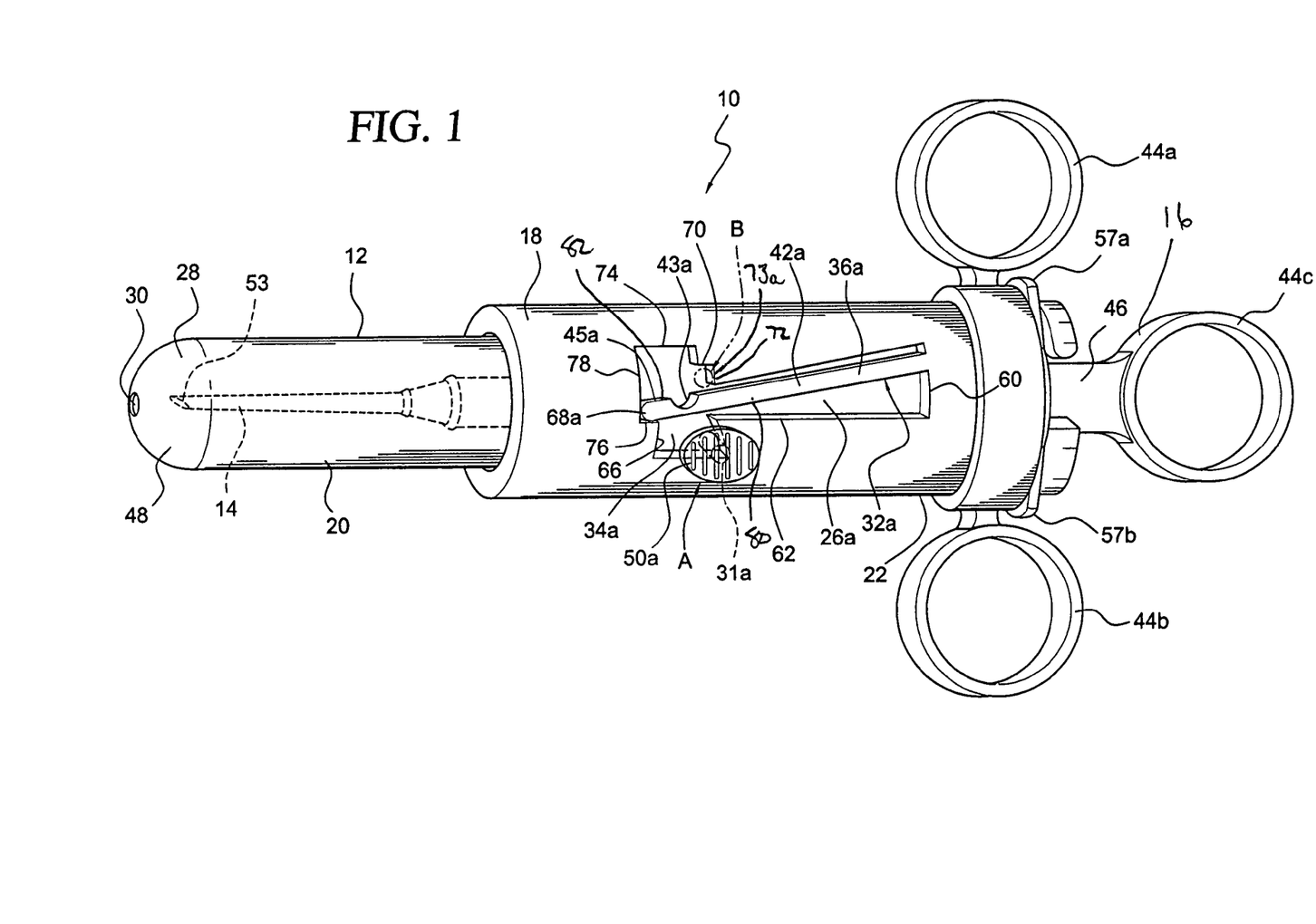
FIG. 1 is a side perspective view of the present needle stick protection device.
Figure 2:
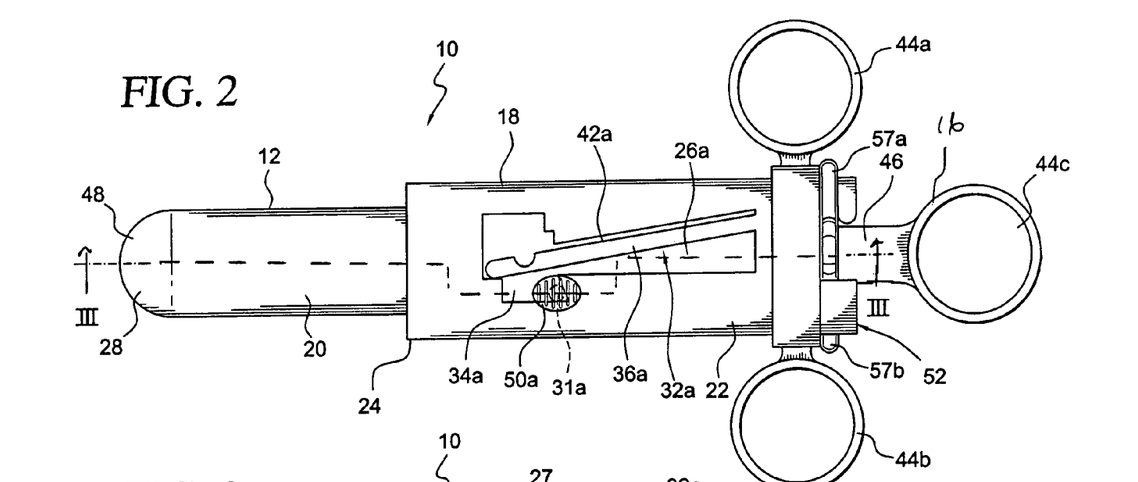
FIG. 2 is a side view of the needle stick protection device with the needle covered.
Figure 3:
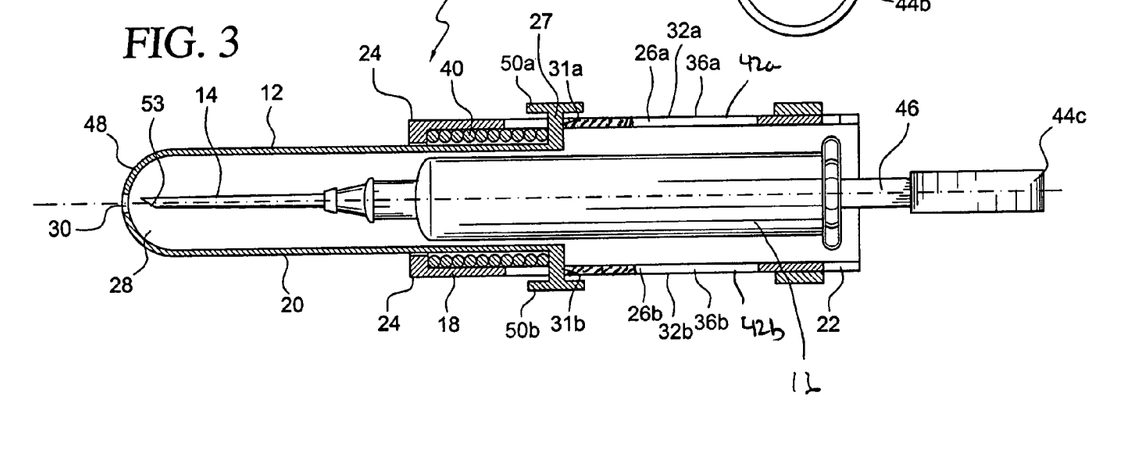
FIG. 3 is a cross sectional view of the needle stick protection device shown in FIG. 2.
Figures 4, 5:
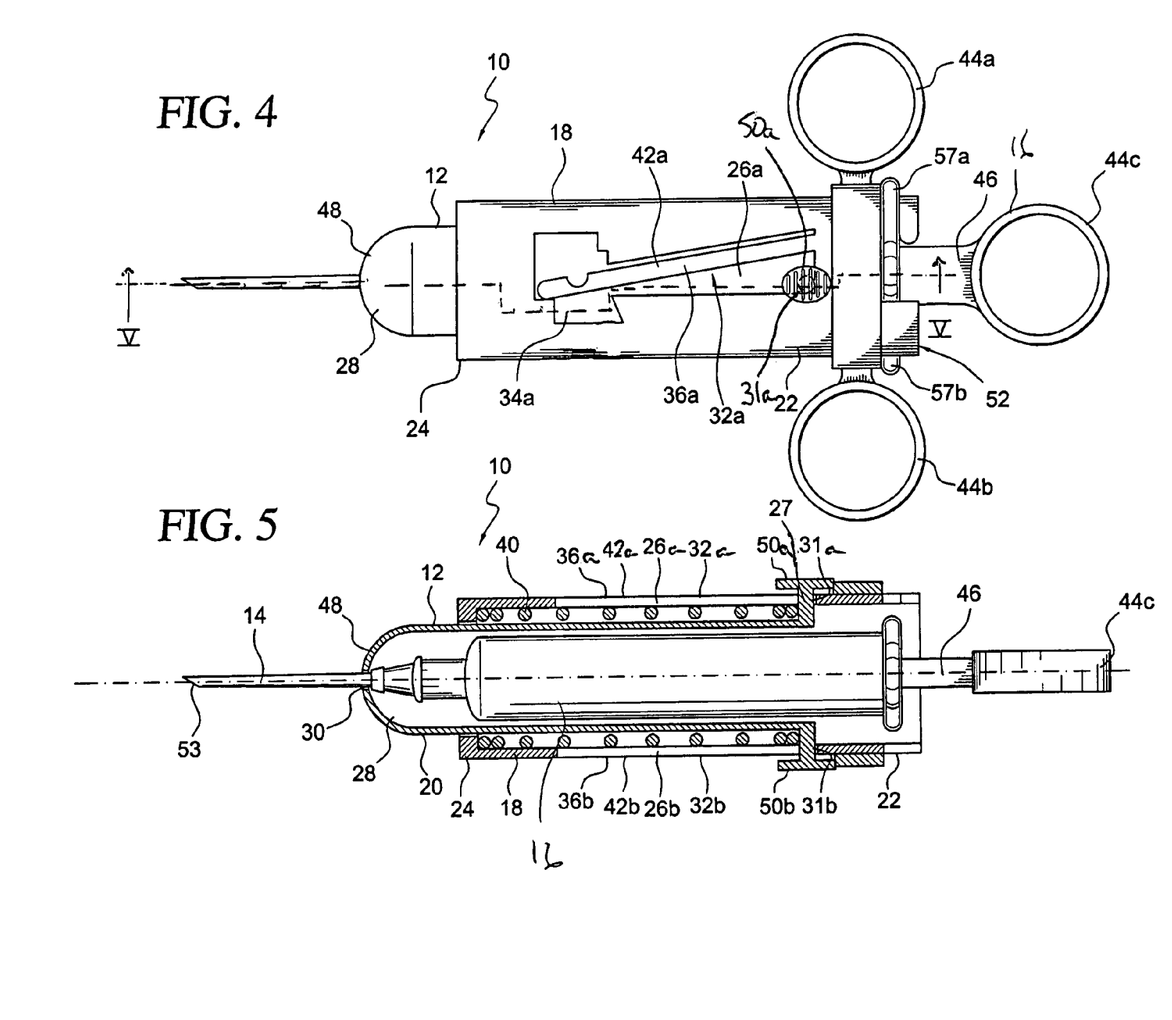
FIG. 4 is a side view of the needle stick protection with the needle exposed.
FIG. 5 is a cross sectional view of the needle stick protection device shown in FIG. 4.
Figure 6:
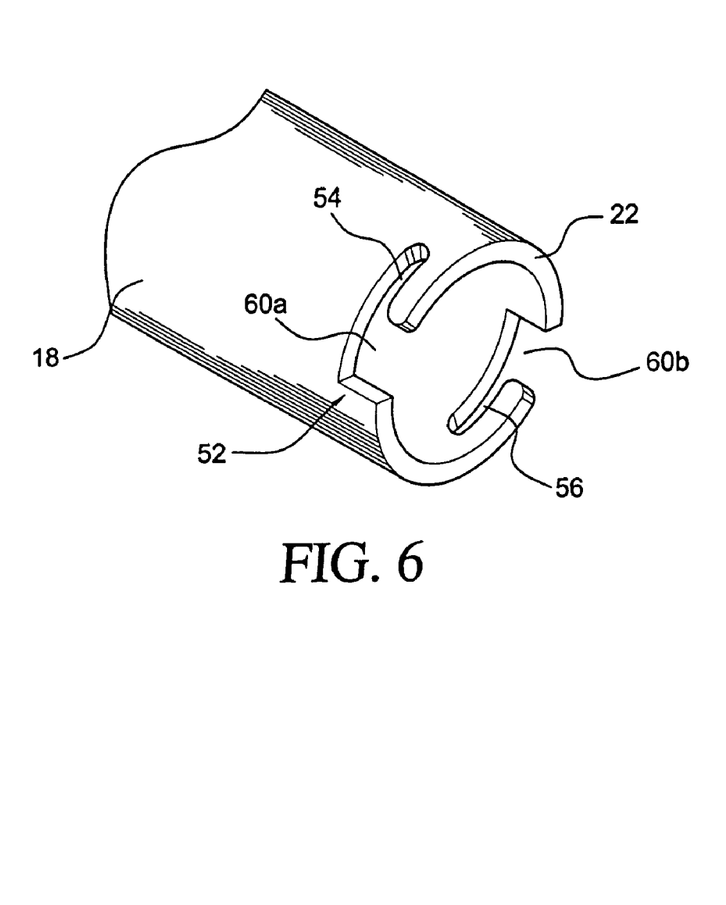
FIG. 6 is a detailed perspective view of the first housing member showing the closure portion.
Figure 7:
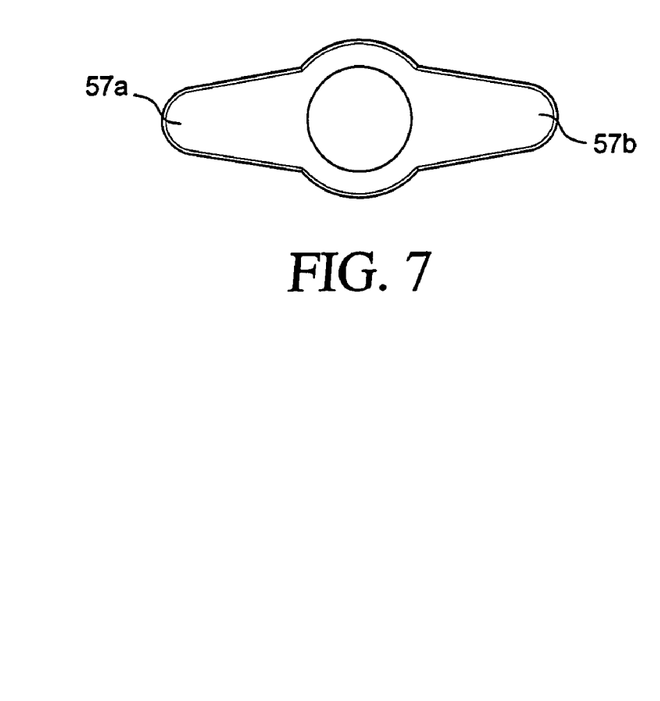
FIG. 7 is a detailed top view showing the opposed ears of the syringe.
Figure 8:
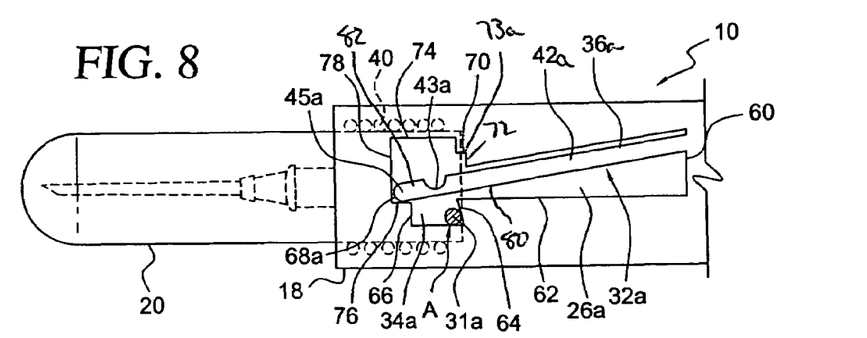
FIGS. 8 to 11 show the steps in operation of the present needle stick protection device.
Figure 9:
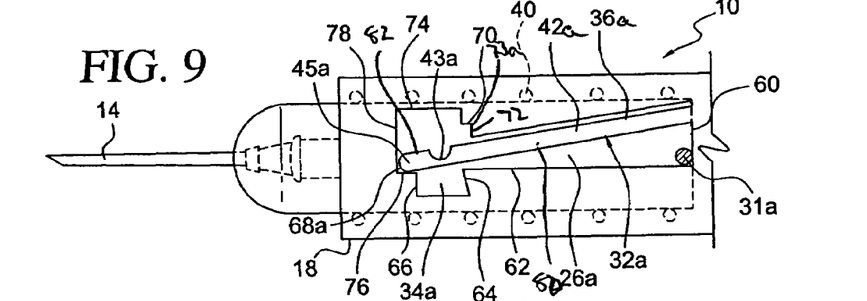
Figure 10:
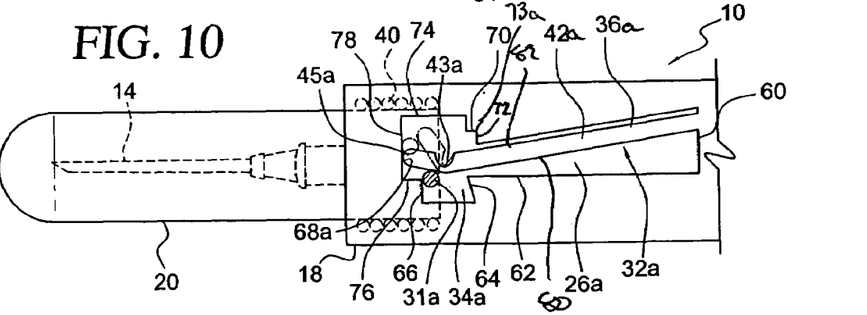
Figure 11:
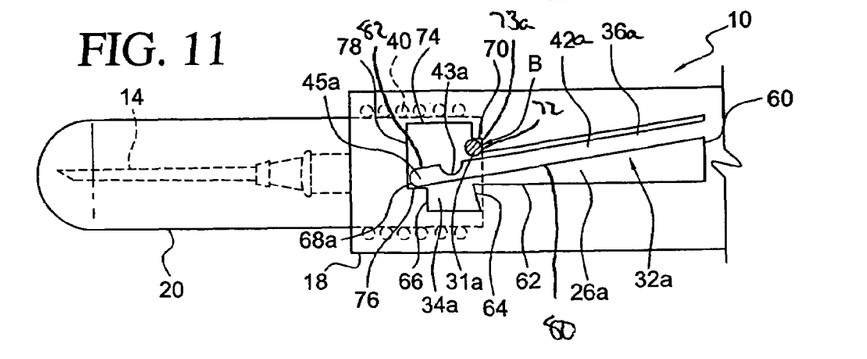
Figure 12:
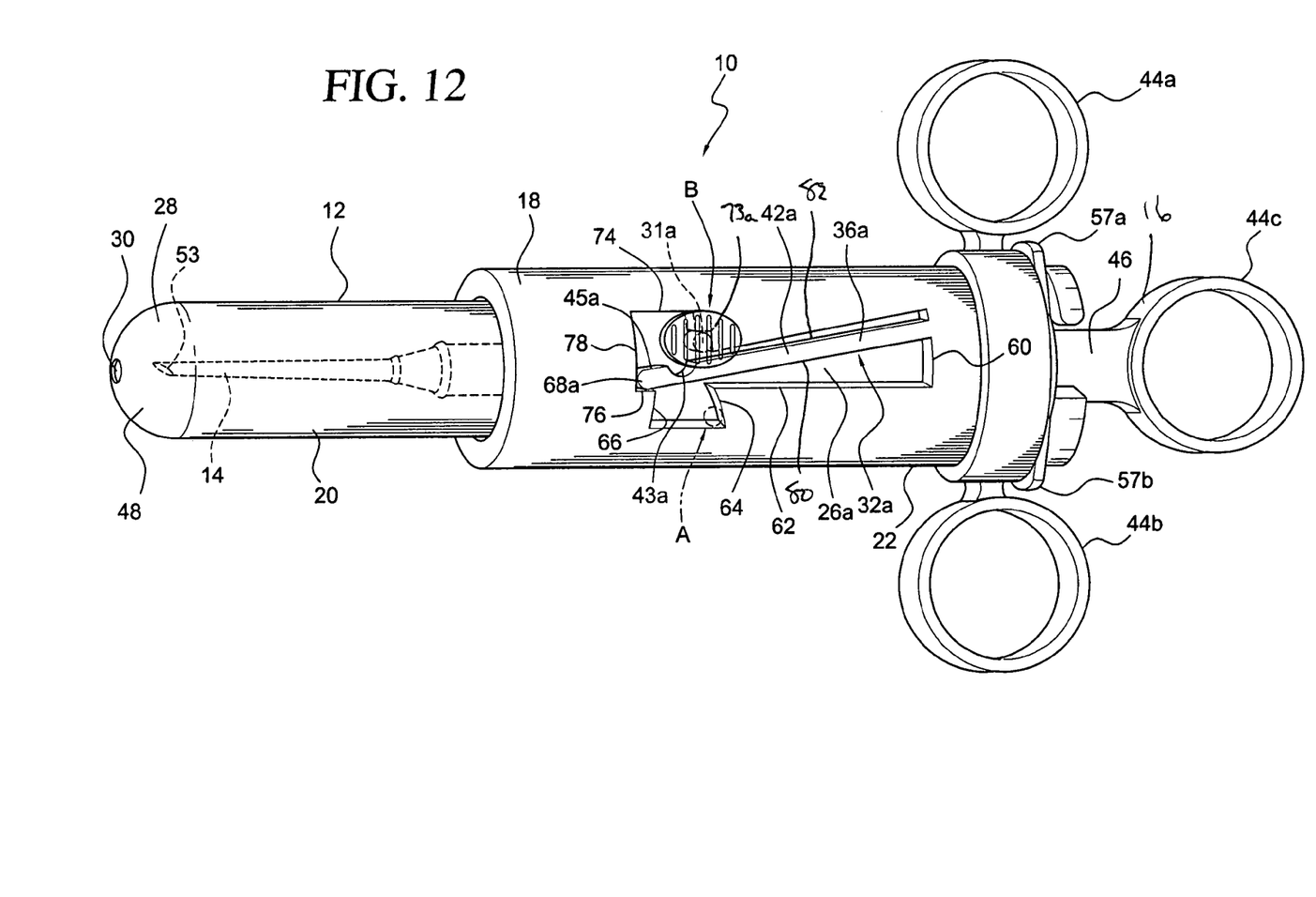
FIG. 12 is a side perspective view of the needle stick protection device in its permanently locked orientation.

The present needle stick protection device 10 provides a mechanism by which the needle 14 may be shielded and unshielded by the physician in a controlled manner and whenever so required by the physician. As such, this can be done repetitively as often as required by the physician during a medical procedure. The locking mechanism of the present needle stick protection device 10 also provides for permanent shielding of the needle 14 once a procedure is completed. As a result, once the needle 14 is permanently shielded in accordance with this embodiment, the needle stick protection device 10 is ready for disposal in a suitable container. Each locking member 32a, 32b includes a lateral retaining recess 34a (only one shown although they are identical) formed within the slot 26a, 26b for selectively seating of the detent 31a, 31b when the second housing member 20 is in its forward most position and a spring biased lock arm 36a, 36b biasing the detent 31a, 31b within the lateral retaining recesses 34a when the second housing member 20 is in its forward most position (see FIGS. 1, 2 and 3). Each slot 26a, 26b also includes a lateral locking recess 73 (only one shown although they are identical) formed within the slot 26a, 26b for selectively permanent seating and locking of the detent 31a, 31b when the second housing member 20 is in its forward most position (see FIG. 2).

The construction of the present needle stick protection device 10 employs a distinctive locking structure. In particular, locking members 32a, 32b are associated with each of the slots 26a, 26b of the first housing member 18 for selectively engaging the respective detents 31a, 31b to control positioning of the second housing member 20 relative to the first housing member 18. Each of the locking members 32a, 32b includes a spring biased lock arm 36a, 36b composed of cantilevered beam 42a, 42b having a living hinge portion 43a, 43b adjacent its free end 45a, 45b. As will be appreciated based upon the following disclosure, this creates a flexible tip 68a, 68b at the free end 45a, 45b of the spring biased lock arm 36a, 36b which permits flexion of the tip 68a, 68b about the living hinge portion 43a, 43b in a manner discussed below in greater detail. The purpose of the living hinge 43a, 43b is to provide easy bending of tip 68a, 68b about the living hinge portion 43a, 43b of the spring biased lock arm 36a, 36b. In addition to functioning in the locking of the present device 10, the interaction between the detents 31a, 31b and the slots 26a, 26b keeps the first and second housing members 18,20 aligned and limits the relative travel between the first and second housing members 18, 20.

In use, the second housing member 20 moves relative to the first housing member 18 to facilitate retraction and extension of the needle 14 through the aperture 30 of the second end 28 of the second housing member 20. With this in mind, the second housing member 20 is hand biased relative to the first housing member 18 in a manner forcing the first end 27 of the second housing member 20 away from the first end 22 of the first housing member 18 to maintain the second housing member 20 in a covered position in which the needle 14 is fully contained within the housing 12; that is, the detent 31a, 31b is forced within the recess 34a to selectively maintain the second housing member 20 in its covered position.

The manually operated second housing member 20 is axially driven by a coil spring 40 relative to the first housing member 18 such that the second housing member 20 covers and uncovers the entire needle 14 with the spring 40 forcing the housing member 20 to an uncovered orientation. The second housing member 20 is automatically locked in position relative to the first housing member 18 by the spring biased lock arms 36a, 36b in the form of one or more cantilevered beams 42a, 42b to provide positive needle stick protection when the second housing member 20 is in its fully extended position. The present needle stick protection device 10 is designed to work with a conventional three-finger syringe arrangement 44a-c commonly utilized within the industry and thereby provides the ability to push and pull on the syringe plunger 46. By using transparent plastic in the construction of the present needle stick protection device 10, the device 10 enables the physician to readily see the contents of the syringe 16.

With regard to the housing 12, and in particular the second housing member 20, it is essentially a cylindrical tube which is open at the first end 27 and has a integral, hemispherical closure 48 at the second end 28. The hemispherical closure 48 has a centrally located aperture 30 through which the needle 14 can freely pass as the second housing member 20 is moved axially to cover and uncover the needle 14. The open first end 27 of the second housing member 18 is fitted with slide actuating portions 50a, 50b for example, pins, cylindrical thumb pads, etc., which are used to manually extend the second housing member 20 so that it covers the entire needle 14. In accordance with a preferred embodiment, the slide actuating portions 50a, 50b are thumb pads which extends from the respective detents 31a, 31b passing through the slots 26a, 26b. The thumb pads 50a, 50b permit ready manipulation of the detents 31a, 31b and the second housing member 20.

The second housing member 20 is locked in place by the interaction of the spring biased lock arms 36a, 36b and the detents 31a, 31b, in conjunction with the retaining recesses 34a and the locking recess 73a, to provide needle protection in the manner discussed below in detail. As the second housing member 20 slides axially to cover the needle tip 53, each of the spring biased lock arms 36a, 36b are deflected by the respective thumb pads 50a, 50b and the detents 31a, 31b used to slide the second housing member 20.

More particularly, the detents 31a, 31b of the second housing member 20 interact with the spring biased lock arm 36a, 36b and the slot 26a, 26b to limit relative travel between the first and second housing members 18, 20. Although the following disclosure only discusses one of the locking members 32a, both locking members 32a, 32b are identical and those skilled in the art will appreciate they function in a similar manner.

In particular, and as will be discussed below in greater detail, when the detent 31a is in the location designated A adjacent the first side 80 of the spring biased lock arm 36a, the present device 10 may be shielded and unshielded by movement of the first housing member 18 relative to the second housing member 20. When the detent 31a is located in location B, the present device 10 is locked and ready for disposal in a suitable container.

In use, and as shown with reference to FIGS. 8 to 11, when the detent 31a is in location A adjacent the first side 80 of the spring biased lock arm 36a, the needle 14 is shielded by the second housing member 20. To unshield the needle 14, the detent 31a is rotated manually clockwise a few degrees until it displaces the spring biased lock arm 36a sufficiently for the spring bias of the lock arm 36a and the spring 40 to drive the detent 31a into contact with a first transverse surface 60. For the purpose of describing the surfaces of the slots 26a, the terms "transverse" and "parallel" are used to designate their orientation relative to the longitudinal axis of the device. To shield the needle 14, the procedure is reversed. The detent 31a is moved along a first parallel surface 62. When it reaches the end of the first parallel surface 62, it is deflected by the spring biased lock arm 36a and the deflection force drives the detent 31a into the circumferentially located lateral retaining recess 34a and toward the recessed contact surface 64 at position A. The contact surface 64 is an obliquely oriented wall substantially preventing undesired movement of the detent 31a from position A. The needle 14 is now shielded. This procedure may be repeated as determined by the physician during the medical procedure by simply rotating the first housing member 18 relative to the second housing member 20 such that the detent 31a is moved out of the retaining recess 34a and the recessed contact surface 64 and returned to the transverse surface 60 where the needle is unshielded. When the alignment is achieved, the compressed coil spring 40 positioned between the first and second housing members 18, 20 automatically returns the second housing member 20 to the axial location at which the needle 14 is uncovered (with the detent 31a positioned against surface 60). Thus, the second housing member 20 can be used to cover and uncover the needle 14, as required by the physician, so that needle sticks are prevented when the present needle stick protection device 10 is passed back and forth between physician and medical technicians.

When the medical procedure is completed, the device 10 is locked for disposal by moving the detent 31a, forward to second transverse surface 66. Then the detent 31a is moved to the right along the second transverse surface 66, a second parallel surface 76, a third transverse surface 78 and a third parallel surface 74 to deflect the tip 68a of the spring biased lock arm 36a via the tip living hinge 43a so that the detent 31a is now adjacent the second side 82 of the spring biased lock arm 36a. The spring 40 interposed between the first housing member 18 and the second housing member 20 then drives the second housing member 20 relative to the first housing member 18 to move the detent 31a into third parallel contact surface 70 and fourth transverse contact surface 72 (defining the locking recess 73a) which lock the needle shield device 10, and in particular, the second housing member 20, in place for disposal of thereof. Once the detent 31a is in location B it cannot be returned to position A by the user, since second parallel surface 76 sits adjacent the first side 80 of the spring biased lock arm 36a and will not permit bending of the tip 68a of the spring biased lock arm 36a in that direction. As a result, the device 10 is locked in the shielded configuration. The device 10 is now ready for disposal using conventional means.

As those skilled in the art will appreciate with reference to the various figures, the spring biased lock arm 36a is not oriented along the axis of symmetry of the syringe 16. However, the spring biased lock arm 36a may be located parallel to the axis of symmetry of the syringe 16 if desired by merely tapering the slot surfaces portion so that the spring biased lock arm must be deflected slightly in order to force the detent 31a into its location along portion 64.

A closure portion 52 is selectively coupled to the finger holes 44b, 44b and is permanently affixed to the first end 22 of the first housing member 18. The first housing member 18 is also adapted to constrain the coil spring 40 used in retracting the second housing member 20 and uncovering the needle 14.

The spring biased lock arms 36a, 36b are an integral part of the first housing member 18. They are designed to produce circumferential forces on the detent 31a, 31b, as the detent 31a, 31b are manually moved along the slots 26a, 26b. When the detent 31a, 31b reach the circumferentially located recesses 34a, the spring biased lock arms 36a, 36b force the detents 31a, 31b into the recess 34a, so that the second housing member 20 cannot be moved relative to the first housing member 18, thereby providing needle stick protection. When the thumb pads 50a, 50b are manually moved out of the recesses 34a, through the application of finger pressure in appropriate directions to overcome the bias of the spring biased lock arms 36a, 36b, the compressed coil spring 40 returns the second housing member 20 to the position where the needle 14 is uncovered.

In accordance with preferred embodiments of the present invention, two design configurations are contemplated for use in conjunction with the helical compression spring 40. Specifically, and in accordance with preferred embodiments of the present invention, the following criteria are contemplated for use in conjunction with the first and second springs:

|  | Spring 1 | Spring 2 |
| --- | --- | --- |
| Wire Gage | 18 Ga | 17 Ga |
| Wire Diameter | 0.047" | 0.054" |
| Mean Coil Diameter | 0.827" | 0.802" |
| Coil Pitch | 0.151" | 0.14" |
| Number of Active Cells | 15 | 16 |
| Unloaded Spring Length | 2½" | 2½" |
| Spring Rate | 0.82#/in. | 1.45#/in. |
| Loaded Deflection | 1½" | 1½" |
| Spring OD When Compressed to Solid | 0.877" | 0.860" |
| Solid height for springs with ground ends | 0.783" | 0.964" |
| Solid height for springs with unground ends | 0.830" | 1.018" |

As mentioned above, the device 10 further includes a closure portion 52 affixed to the first end 22 of the first housing member 18. The closure portion 52 is cylindrical and is shaped and dimensioned to be permanently affixed at the first end 22 of the first housing member 18. Adjacent two slots 54, 56 at 180° are formed in the first housing member 18. The geometry of the slots 54, 56 is such that the ears 57a, 57b of the syringe 16 are held in place by an interference fit. The syringe 16 is placed into the recesses 60a, 60b in the first housing member 18 and rotated circumferentially to lock the ears 57a, 57b of the syringe to the first housing member 18 thereby locking the syringe 16 in the needle stick protection device 10. The syringe 16 may be locked in place using finger pressure. The two lateral finger holes 44a, 44b are permanently affixed to the closure portion 52 and are located at 90° from the slots 54, 56 in the first housing member 18 and 180° from each other.

In use, the present needle stick protection device 10 can be completely assembled and will function with or without the syringe 16 in place. The entire syringe 16 with the needle 14 attached is placed in the needle stick protection device 10 and is locked in the first housing member 18. The physician can then expose the needle 14 as described above, insert the needle 14 into the patient as many times as necessary, shielding and unshielding the needle 14 each time it is transferred back and forth between the physician and the medical technician. As mentioned above, since the needle stick protection device is made of transparent plastics, the physician can readily determine when the needle is in a blood vessel by slightly withdrawing the syringe plunger.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A needle stick protection device, comprising:
a housing shaped and dimensioned for positioning about a syringe with an attached needle, the housing includes a first housing member telescopically coupled to a second housing member;
the first housing member including an open first end shaped and dimensioned for receiving the syringe and attached needle and an open second end, the first housing member including a first longitudinally extending slot;
the second housing member including an open first end and a substantially closed second end, the second end including an aperture shaped and dimensioned to permit the passage of a needle therethrough, the second housing member including a first detent extending through the first slot; a locking member associated with the first slot of the first housing member for selectively engaging the first detent to control positioning of the second housing member relative to the first housing member; the locking member includes a first lateral retaining recess formed within the first slot for seating of the first detent when the second housing member is in its forward most position, the first lateral retaining recess being circumferentially located along a side of the first slot, and the locking member further includes a first spring biased lock arm composed of a cantilevered beam, which includes a first side that is adjacent to the first lateral retaining recess, wherein the spring biased lock arm circumferentially forces the first detent within the first lateral retaining recess when the second housing member is in its forward most position fully extended relative to the first housing member so that the needle is fully covered by the second housing member; wherein the needle may be selectively covered and uncovered by selective alignment of the first detent with the slot in a manner permitting controlled motion of the first housing member relative to the second housing member; and the locking member further includes a lateral locking recess formed along the slot and adjacent a second side of the spring biased lock arm opposite the first side of the spring biased lock arm, wherein the needle is permanently covered when the detent is positioned within the lateral locking recess, wherein the spring biased lock arm includes a living binge portion adjacent its free end creating a flexible tip at the free end of the spring biased lock arm which permits flexion of the tip about the living hinge portion in a manner allowing the detent to move from the first side of the spring biased lock arm to the second side of the spring biased lock arm.

2. The needle stick protection device according to claim 1, wherein the slot, on the first side of the spring biased lock arm, includes a first transverse surface, a first parallel surface, an oblique contact surface, a second transverse surface and a second parallel surface adjacent a tip of the spring biased lock arm.

3. The needle stick protection device according to claim 2, wherein the second parallel surface prevents the tip from bending in a manner permitting the detent to move from the second side of the spring biased lock arm to the first side of the spring biased lock arm.

4. The needle stick protection device according to claim 3, wherein the oblique contact surface and the transverse surface define the first lateral retaining recess.

5. The needle stick protection device according to claim 4, wherein the slot, on the second side of the spring biased lock arm, includes a third transverse surface, a third parallel surface, as well as a fourth parallel surface and fourth transverse surface defining the lateral locking recess.

6. The needle stick protection device according to claim 3, wherein the slot, on the second side of the spring biased lock arm, includes a third transverse surface, a third parallel surface, as well as a fourth parallel surface and a fourth transverse surface defining the lateral locking recess.

7. The needle stick protection device according to claim 2, wherein the oblique contact surface and the transverse surface define the first lateral retaining recess.

8. The needle stick protection device according to claim 1, wherein the first housing member further includes a second longitudinally extending slot and the second housing member further includes a second detent extending through the second slot.

9. The needle stick protection device according to claim 8, wherein the locking member further includes a second lateral retaining recess formed within the second slot for seating of the second detent when the second housing member is in its forward most position and a second spring biased lock arm biasing the second detent within the second lateral recess when the second housing member is in its forward most position.

10. The needle stick protection device according to claim 9, wherein the first and second spring biased lock arms are respective cantilevered beams.

11. The needle stick protection device according to claim 1, wherein the first housing member includes means for selectively attaching to a syringe.

12. The needle stick protection device according to claim 11, wherein the means for selective attachment includes a pair of opposed slots at the first end of the first housing member, the opposed slots being shaped and dimensioned for receipt of the syringe.

13. The needle stick protection device according to claim 1, wherein the slot, on the first side of the spring biased lock arm, includes a first transverse surface, a first parallel surface, an oblique contact surface, a second transverse surface and a second parallel surface adjacent a tip of the spring biased lock arm.

14. The needle stick protection device according to claim 1, wherein the slot, on the second side of the spring biased lock arm, includes a third transverse surface, a third parallel surface, as well as a fourth parallel surface and fourth transverse surface defining the lateral locking recess.

15. The needle stick protection device according to claim 1, further including a spring positioned between the second end of the first housing member and the first end of the second housing member, the spring urging the first housing member and the second housing member to a fully telescoped position in which the needle is exposed.

16. The needle stick protection device according to claim 1, wherein the second housing member further includes a slide actuating portion secured to the first detent of the second housing member facilitating controlled movement of the second housing member relative to the first housing member.

17. The needle stick protection device according to claim 1, wherein the housing is transparent.

18. The needle stick protection device according to claim 1, wherein the slide actuating portion is a thumb pad.

* * * * *